US012064367B2

(12) United States Patent
Romo et al.

(10) Patent No.: US 12,064,367 B2
(45) Date of Patent: Aug. 20, 2024

(54) ADJUSTMENT SYSTEM

(71) Applicant: Ossur Iceland ehf, Reykjavik (IS)

(72) Inventors: Harry Duane Romo, Foothill Ranch, CA (US); Matthew Barrientos, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 90 days.

(21) Appl. No.: 16/750,352

(22) Filed: Jan. 23, 2020

(65) Prior Publication Data

US 2020/0229960 A1 Jul. 23, 2020

Related U.S. Application Data

(60) Provisional application No. 62/795,673, filed on Jan. 23, 2019.

(51) Int. Cl.
*A61F 5/02* (2006.01)
*A61F 5/01* (2006.01)

(52) U.S. Cl.
CPC .............. *A61F 5/02* (2013.01); *A61F 5/0123* (2013.01)

(58) Field of Classification Search
CPC ...... A61F 5/0123; A61F 5/01; A61F 5/02–03; A61F 5/0102; A61H 1/0281; A61H 1/0274; A61H 2201/1628; A61H 2201/1638; A61H 2201/165; A61H 1/02; A61H 2201/16; A61H 2201/1602; A61H 2201/1619–1652; A43C 11/00; A43C 11/16; A43C 11/165; A43C 11/20; A43C 11/22
See application file for complete search history.

(56) References Cited

U.S. PATENT DOCUMENTS

| | | | | |
|---|---|---|---|---|
| 5,181,331 A | * | 1/1993 | Berger | A43C 11/16 24/712.1 |
| 5,857,988 A | * | 1/1999 | Shirley | A61F 5/0125 602/26 |
| 2011/0215601 A1 | * | 9/2011 | Mueller | B66C 1/12 294/74 |
| 2013/0184628 A1 | * | 7/2013 | Ingimundarson | A61F 5/0125 602/26 |
| 2016/0287424 A1 | * | 10/2016 | Webster | A61F 5/055 |
| 2019/0231576 A1 | * | 8/2019 | Lawrence | A61F 5/028 |

* cited by examiner

*Primary Examiner* — Michelle J Lee
(74) *Attorney, Agent, or Firm* — Workman Nydegger

(57) ABSTRACT

An adjustment system is arranged to be mounted on a frame of a body interface, and includes a tensioning device in cooperation with a tensioning element, at least one elastic component, and at least one connector. The adjustment system can adjust at least one of the connectors, which in turn may carry additional components such as assistive devices in an exoskeleton device, assistive device, orthopedic device, or prosthetic device.

13 Claims, 5 Drawing Sheets

ADJUSTMENT SYSTEM

FIELD OF THE DISCLOSURE

The disclosure relates to the field of adjustment systems, and more particularly to an adjustment or tensioning system for applying tension for at least one component over a structure, such as for body interfaces for exoskeletons or assistive devices, orthopedic devices or prosthetic devices.

BACKGROUND

Exoskeleton devices and body interfaces for the same are an increasingly important field of technology, as exoskeleton devices have the potential to help humans conduct various activities in a safer, more efficient, and more comfortable manner. In certain manufacturing settings, workers must conduct physically demanding and precise tasks involving heavy and/or dangerous objects and/or awkward or precarious positions, often in a repetitive fashion and for hours at a stretch. Without the assistance of an exoskeleton device, workers may become fatigued or uncomfortable, leading to errors, low productivity, and possibly even injury. Exoskeleton devices may also enable aging workers with valuable skills and experience to continue to work in a physically demanding field for a longer period than might be otherwise possible.

Exoskeleton devices are useful for supplementing the natural strength and motions of a human body to provide strength, support, and comfort. Exoskeleton devices may have an independent power supply or passive or energy-storage devices, enabling the exoskeleton device to do the "heavy lifting" for a human user through the function of actuators or other motion-assistive components. For example, an exoskeleton device may help a user to hold steadily a heavy tool so the user can focus their attention on using the tool to perform precision and/or repetitive work.

In other cases, exoskeleton devices may be configured to provide relief when a human user is working in an uncomfortable position or can provide posture improvement. A surgeon may benefit from an exoskeleton device that relieves the surgeon of the effort of holding their arms in a certain position over a patient throughout the duration of a surgical operation or that helps the surgeon to lean over a patient in what would otherwise be an awkward or uncomfortable position for extended periods of time without fatigue or discomfort. A manufacturing technician may benefit from an exoskeleton device holding their arms up or maintaining their posture as they work on a piece of equipment, especially when the technician is performing work in an awkward or uncomfortable position, such as standing underneath the piece of equipment.

Other beneficial arrangements include the provision of additional sets of hands, improved balance, strengthened grip, stabilization of movements, shock absorption, muscle memory, and others.

In existing exoskeleton devices and assistive devices, such as orthopedics and prosthetics, recreational equipment and sports equipment, a body interface is needed to couple the exoskeleton device or assistive device to a user's body. Because individual users' dimensions are varied, providing a body interface that comfortably and precisely couples an exoskeleton device or assistive device to a specific user is a challenge. Similarly, providing a body interface that intuitively couples the exoskeleton to a user provides a further challenge, as misuse or misalignment of the body interface to a user's body can lead to discomfort, poor compliance, failure of the interface and/or the exoskeleton device, and other adverse effects.

The body interface is weight bearing because it often supports components, such as assistive devices, and/or supports a user's weight during movement. It is important in a body interface that it can remain stable despite load-bearing and activation of assistive devices so as not to incur stress or exert loads on the user. The body interface is provided to distribute loads in a comfortable and non-exhaustive manner to the user.

The ability to adequately and intuitively vary the configuration of components of a body interface for an exoskeleton device or other assistive device is important in settings where one user may wear the body interface and exoskeleton device during a shift or a procedure, and a second user may wear the same body interface in a later or subsequent shift or procedure. Adjustability is also valuable as a single configuration can be provided to easily conform a device to a user with minimized customization. In other settings, an exoskeleton device may perform a plurality of functions, with different configurations of the body interface pertaining to different functions.

There is a challenge for body interfaces to have adjustment systems for simply, repeatedly, and effectively adjusting the size of the components to the subsequent or specific user's dimensions. Due to the increasing complexity of exoskeleton devices and interfaces adapted for use therewith, the number of adjustments a user may have to make for proper fit may be substantial.

Navigating the tension between providing a structurally robust body interface and providing a comfortable, minimal-weight, flexible body interface is further a challenge, as heavier components can lend strength but can also make the body interface more cumbersome to use and costly to produce and obtain.

Orthopedic devices, such as knee braces, may comprise components that function best when sized to a user's needs or dimensions, which may be dynamic during use. There is a problem of existing orthopedic devices providing insufficient, costly, and/or difficult-to-use adjustment systems to allow the orthopedic device to conform to the user. A user may be required to operate and individually adjust several straps, including force straps, to fit the device. This can be cumbersome and imprecise as the user may have to make such adjustments often during use. There is accordingly a need for an adjustment system allowing for simplified, intuitive, and more accurate adjustment of straps and other components in orthopedic, prosthetic, medical, and other devices.

Adjustment or tensioning systems are useful for sizing and adjusting components in many devices. Tensioning systems may be adapted to alter the configuration and size of certain attachment elements or components to fit a specific user's dimensions. Tensioning systems may apply a variable amount of pressure or size-adjustment in response to a user's selection. There is a need for adjustment or tensioning systems arranged to alter the configuration of a device such as a body interface effectively, such that a user's dimensions are properly met, and intuitively, such that normal users are able to adjust, don, and use the device without undue complication. It is also desirable to minimize the cost of a body interface and adjustment systems provided therewith by minimizing the number of tensioning systems required to adjust the configuration of a body interface.

Adjustment or tensioning systems may apply tension to adjust a configuration or size of attachment elements or components along a spectrum rather than a few discrete settings, leading to difficulty in repeatedly and consistently attaining a desired size or configuration of the attachment elements. There is a need for an adjustment system for multiple components that provides an intuitive indication to a user of a degree of tension required to attain a proper and/or predetermined configuration.

For at least these reasons, there is a need for an improved adjustment or tensioning system provided with a body interface, orthopedic device, or other device that overcomes the shortcomings of known adjustment or tensioning systems and methods of adjusting the same.

SUMMARY

According to an embodiment provided herein, an adjustment system is provided on a structure, in an exemplary form of a body interface, that may cooperate with an exoskeleton device or other assistive device to accurately and intuitively apply tension to adjust one or more components to the unique and dynamic dimensions, functional requirements, and comfort of individual users. The adjustment system addresses the aforementioned problems of structures for individual use by providing a simple method and system for tensioning, and thereby adjusting the configuration of one or more components on a structure simultaneously and/or because of singular regulation by a user. By so doing, the cost to produce and obtain the structure and tensioning system is reduced as fewer tensioning and adjustment systems overall are required.

The adjustment effected by the adjustment system is provided while not interfering with the components and/or load bearing of the structure or body interface. Adjustment can be done while the body interface is in operation with assistive devices without modifying or adversely affecting the mode of operation of the body interface and assistive devices, and while maintaining generally constant load-bearing and functionality.

In an embodiment, the ease of using the adjustment system may be enhanced as a user need only regulate a single tensioning device to accurately and consistently adjust the configuration of one or more attachment components for ease and predictability of use. The body interface or corresponding structure provides means for the one or more components to move while maintaining generally constant load-bearing and functionality.

The adjustment system is provided with features such as indicia and terminals that enable a user to ascertain that the one or more attachment components have been adequately placed and adjusted for further ease of use and proper functionality. The elastic elements may be provided with a casing, such as being formed from elastomeric material, that cooperates with the indicia to indicate tension levels and to provide robust support.

The one or more attachment components are adapted to return to a degree of tension and to a predetermined position such that the adjustment system may be repeatedly and reliably be adjusted from a known degree of tension and from a known position. The adjustment system addresses challenges of existing adjustment systems that allow for a user to apply desired amounts of tension at discrete levels.

The adjustment system may be provided with elastic elements that may be configured to permit varying degrees of tension, in single or multiple directions. The regulation of the tensioning device may urge first and second elastic elements to simultaneously move in first and second directions relative to one another upon actuation or adjustment by the adjustment system, for example upon actuation of the tensioning device in a first manner.

In another embodiment of the disclosure, an orthopedic device, a knee brace, is provided with an adjustment system arranged to adjust tension in one or more components, such as straps, simultaneously. The adjustment system may be arranged on a rigid frame or shell of the orthopedic device and tension a cable extending to end portions of at least one strap, with rotation or adjustment of the adjustment system changing a length of the cable to adjust an amount of tension in, or a length of, both straps based on a single act of actuation or adjustment of the tensioning device in a first manner.

The tensioning device accordingly simplifies a process for adjusting components of the orthopedic device and provides for greater accuracy and repeatability of adjustment, while the structure upon which the components are secured can maintain generally a consistent and desired amount of load-bearing and functionality.

These and other features, aspects, and advantages of the present disclosure will become better understood regarding the following description, appended claims, and drawings.

BRIEF DESCRIPTION OF THE DRAWINGS

The adjustment system disclosed in the following drawings is illustrated for example only. The elements and combinations of elements described below and illustrated in the drawings can be arranged and organized differently to result in embodiments still within the spirit and scope of the adjustment system embodiments described herein.

DETAILED DESCRIPTION OF VARIOUS EMBODIMENTS

The embodiments of the disclosure, namely an adjustment system in use with a body interface, orthopedic device, or other device, are adapted for a human body, and may be dimensioned to accommodate different types, shapes, and sizes of human body sizes and contours as well as different intended functionalities of the body interface. For explanatory purposes, the adjustment embodiments described herein correspond to different sections of a body and are denoted by general anatomical terms for the human body.

The embodiments of the adjustment system and body interface are referred to as corresponding to medial and lateral directions defined by a sagittal or median plane. A medial direction is directed to a center of a body, whereas a lateral direction is directed outwardly from a center of the body corresponding to the sagittal or median plane. The embodiments are referred to therefore as corresponding to lateral and medial sides defined by a median or sagittal plane. Upper and lower sections of the adjustment system and body interface are defined according to the normal understanding of "upper" (nearer to the top of the body or the head of the body) and "lower" (nearer to the bottom of the body or the feet relative to the upper direction). The anatomical terms described are not intended to detract from the normal understanding of such terms as readily understood by one of ordinary skill in the art of orthopedics, exoskeleton devices, and human anatomy.

Figure 1:
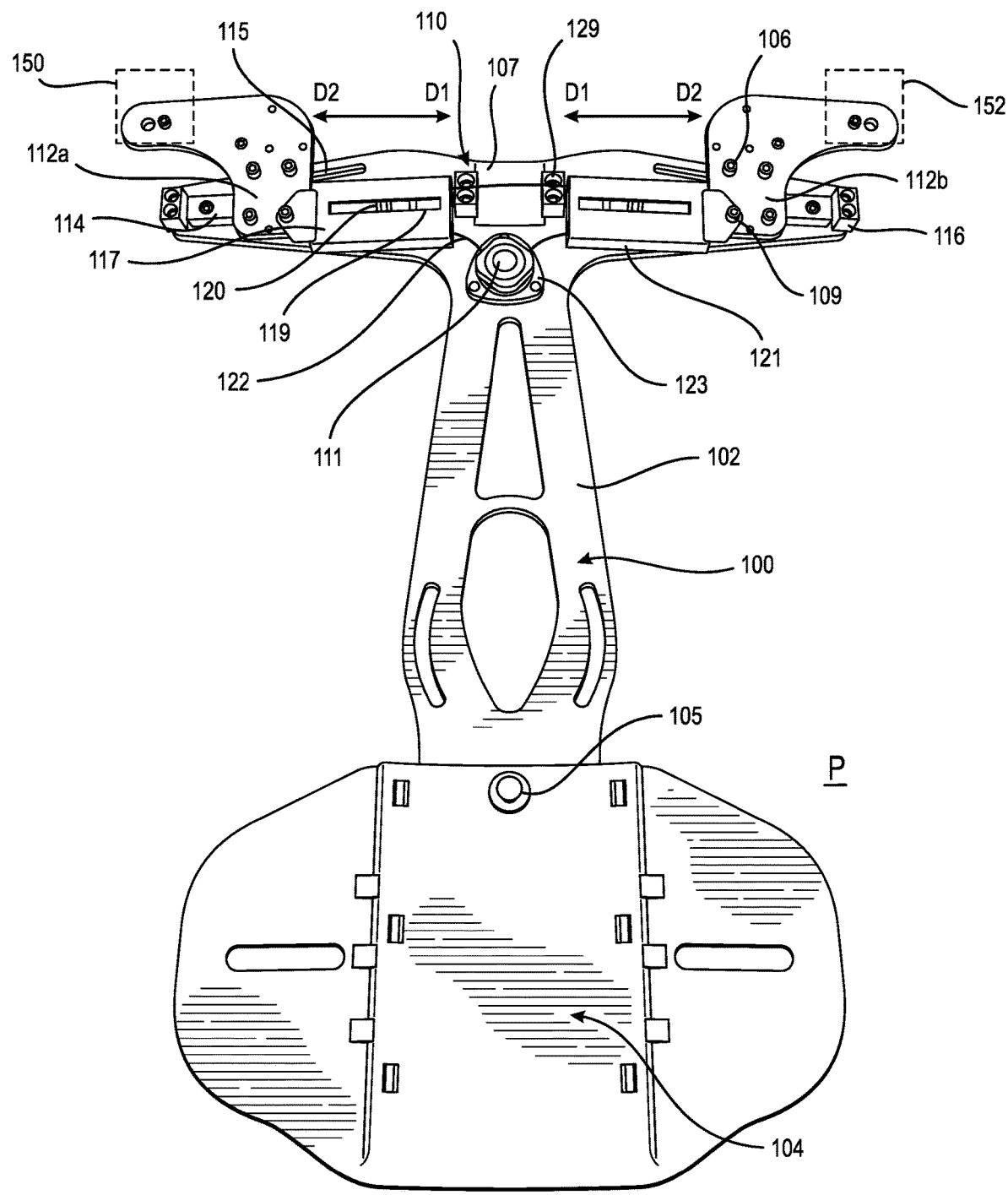
FIG. 1 illustrates a plan view of a posterior or outer side of an embodiment of an adjustment system in a body interface.

FIG. 1 illustrates in plan view a posterior side P, or the outwardly facing side, of a body interface 100 utilizing an adjustment system 110 according to the disclosure. The body interface 100 comprises a frame 102. The frame 102 may advantageously be formed from a material with enough strength to cooperate with an exoskeleton device or other assistive device as a user undergoes physical activities, such as in a workplace. In certain embodiments, the frame 102 may be formed of a rigid yet malleable material, such as aluminum, carbon-fiber components, or other materials, such that the frame 102 may be contoured to adapt to a user's dimensions, as will be described in further detail in the following discussion.

As seen in FIG. 1, the frame 102 may comprise a vertical strut (arranged generally proximate a user's spine), which may be connected to a horizontal strut (arranged generally proximate a user's shoulders). The frame 102 may be connected to a suitable lumbar portion 104 that connects to the frame 102 by a suitable fastener 105, the lumbar portion 104 serving in embodiments to comfortably and reliably anchor and attach the body interface 100 to a user.

Figure 3:
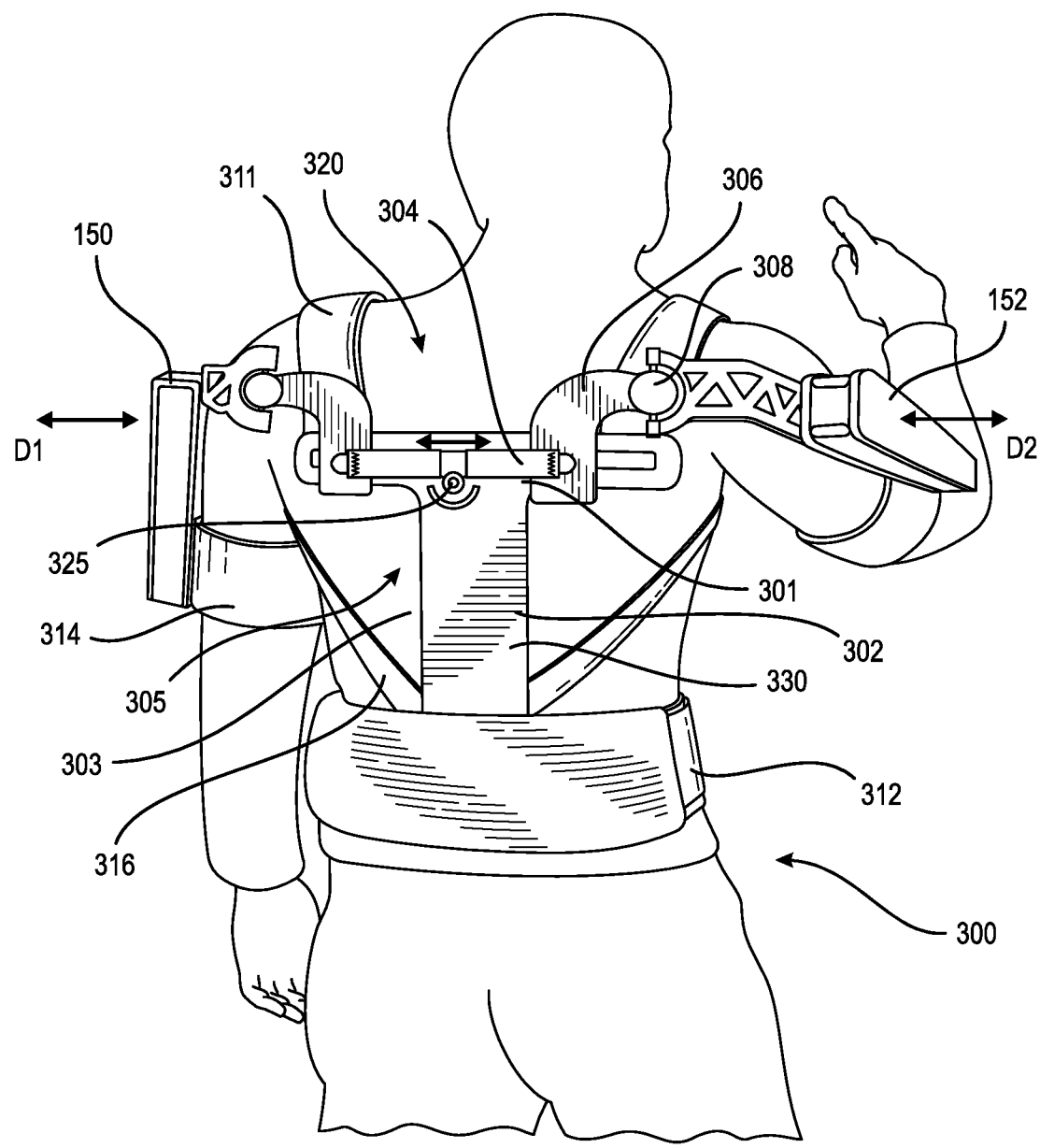
FIG. 3 illustrates a perspective schematic view of an adjustment system in a body interface adapted to cooperate with an exoskeleton device.

First and second assistive devices 150, 152 are connected to first and second sides of the frame 102 via first and second connectors 112a, 112b, and are configured to be correspondingly secured to first and second sides of a user's body and/or arms (i.e., left and right arms). FIG. 1 only shows such first and second assistive devices 150, 152 schematically, although FIG. 3 shows such first and second assistive devices 150, 152 in more detail.

An example of a body interface is found in U.S. Patent application publication no. 2018/0303699, published on Oct. 25, 2018, and an example of assistive devices in found in international patent application publication no. WO 2019/016629, published on Jan. 24, 2019, each of which is incorporated herein by reference. FIG. 3 exemplifies a body interface in combination with assistive devices according to these references.

The adjustment system 110 is arranged on the frame 102, preferably directly on the frame 102 and may be adjustable relative thereto. In the depicted embodiment, the adjustment system 110 is arranged to tension and adjust the configuration of first and second connectors 112a, 112b that connect the assistive devices 150, 152 for a user's arms to the frame 102. The adjustment system 110 is arranged at an upper portion 107 of the frame 102, such that the adjustment system 110 may act on and change a position of the first and second connectors 112a, 112b relative to the frame 102 in the vicinity of a user's back and/or shoulders, as the width of a user's back and shoulders varies widely from person to person. The adjustment system 110 thus helps adjust the body interface 100 to a user's dimensions for optimal effectiveness. The adjustment system 110 advantageously secures the connectors 112a, 112b in an anatomically optimal position, rather than allowing the connectors 112a, 112b to slide, float, or be biased towards a point of lowest resistance.

The adjustment system 110 may utilize a dial tensioning device 111, such as produced by Boa Technology, Inc of Denver, Colorado Examples of tensioning devices are found in U.S. Pat. No. 9,358,146, granted on Jun. 7, 2016; U.S. Pat. No. 10,143,581, granted on Dec. 4, 2018; U.S. patent application publication no. 2017/0348131, published on Dec. 7, 2017; each of which is incorporated herein in its entirety by reference.

Other embodiments of tensioning devices are envisioned, and the adjustment system 110 is not limited to a dial-tensioning device. A tensioning device may be derived from a linear ratcheting system as in U.S. Pat. No. 7,198,610, granted Apr. 3, 2007, and incorporated herein in its entirety by reference. Other types of tensioning devices may likewise be used in which tensioning of at least one tensioning element may be achieved in a predetermined and suitable manner.

Figure 2:
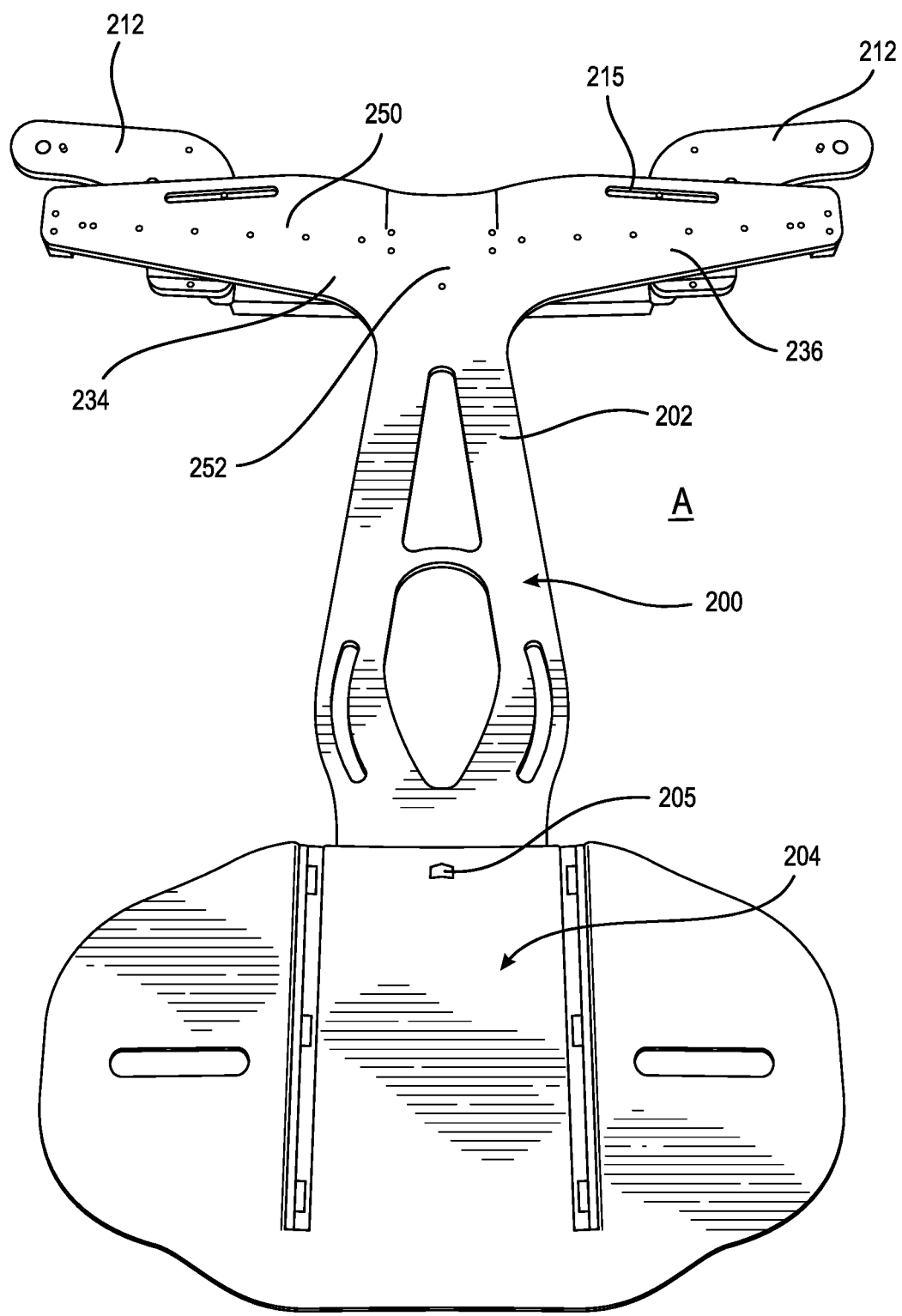
FIG. 2 illustrates a plan view of an anterior or inner side of the embodiment of an adjustment system in a body interface.

The tensioning device 111 is preferably anchored to or supported on the frame 102 by an anchor or platform 123, which may comprise a layer of reinforcing material such as elastomeric material attached to or alternatively overmolded on the frame 102 via apertures 252 (shown in FIG. 2). The tensioning device 111 may comprise a housing and may be arranged to receive and cooperate with an elongate tensioning element 122 in the depicted embodiment by changing a length of the elongate tensioning element 122. The tensioning device 111 may be fixedly secured to the frame 102 so as to anchor the adjustment system when the tensioning device 111 applies tension to the tensioning element 122 and associated components. In embodiments, the tensioning device 111 may be configured to increase the length of at least a segment of the elongate tensioning element 122 upon being actuated in a first manner, and to decrease the length of the segment of the elongate tensioning element 122 upon being actuated in a second manner.

The tensioning device 111 may be locked by the user to prevent accidental increases or decreases in the length of the elongate tensioning element 122. The elongate tensioning element 122 may be inelastic. In other embodiments, the elongate tensioning element 122 may be elastic, or may comprise sections of varying elasticity.

The frame 102 may be rigid or semi-rigid to provide a stable platform for the tensioning device 111 so activation, rotation, and/or regulation of the tensioning device 111 does not alter stability and function of the frame 102. The frame 102 therefore preferably maintains generally constant load-bearing and functionality as the tensioning device 111 is regulated.

The elongate tensioning element 122 may be configured to tension one or more elastic components 117, 121, which are located on first and second sides of the frame 102, respectively, and correspond to the first and second connectors 112a, 112b. The elastic components 117, 121 may define guides 412 (shown in FIGS. 4A-4C) within a body thereof on a first or medial end or side. The guides 412 may be arranged as channels through which the elongate tensioning element 122 may pass as the tensioning device 111 serves to increase or a decrease the length of the elongate tensioning element 122. The guides 412 may comprise reinforcement stitching or other features to securely retain the elongate tensioning element 122. The elastic components 117, 121 may comprise at least one segment of elastic material, or may be formed in a substantial entirety thereof of elastic material.

In the depicted embodiment, the elongate tensioning element 122 is configured to define a circuit between three attachment points: the tensioning device 111, the first or left-side elastic component 117 and the second or right-side elastic attachment component 121. As the tensioning device 111 is actuated to shorten an effective length of the elongate tensioning element 122, and thereby apply tension, the elastic components 117, 121 are elongated or extended beyond an initial predetermined length and drawn medially together in a direction D1, resulting in movement of the first and second connectors 112a, 112b against a lateral or outward bias in a direction D2 from the attachments 150, 152 to which the elastic components 117, 121 may be anchored. In embodiments, the elastic components 117, 121 can be configured to resist movement of the connectors 112a, 112b and to elastically extend away from the initial predetermined length in the direction D2.

Likewise, as the tensioning device 111 is actuated to increase the length of the segment of the elongate tensioning element 122, tension is relieved or reduced, allowing the elastic components 117, 121 to relax or contract back to the predetermined length, and allowing the connectors 112a, 112b to float outwardly in the direction D2. In the depicted embodiment, the connectors 112a, 112b are arranged at least proximate to a portion of the user generally at or past an end of the corresponding elastic component 117, 121 in the direction D2. The elastic components 117, 121 may be configured to bias the connectors 112a, 112b in the first direction D1, as well as to resist movement of the connectors 112a, 112b in the second direction D2. The tensioning device 111 may uniformly adjust the lengths of multiple elastic components 117, 121.

By providing an adjustment system 110 according to the embodiments, the first and second connectors 112a, 112b and accordingly the first and second attachments 150, 152 may be arranged relative to the body interface 100 in a desired or optimal configuration based on the user's dimensions, as opposed to the first and second connectors 112a, 112b receding to a point of least resistance under the lateral or outward bias from the first and second attachments 150, 152.

The attachments 150, 152 may continuously transmit a load via the respective connectors 112a, 112b to the body interface 100 while translating or floating relative thereto on a path defined by or on the body interface 100, as will be described in greater detail herein. The tensioning device 111 can be arranged centrally between the elastic components 117, 121, and the predetermined length of the elastic components 117, 121 may be the same. In embodiments each elastic component 117, 121 may have a unique length and elasticity.

Each of the elastic components 117, 121 may attach at lateral extreme or second ends to a corresponding sleeve 118 which may define a channel or gap in a thickness thereof within which the elastic components 117, 121 may extend. Alternatively, the sleeve 118 may extend about the respective elastic components 117, 121 with the elastic components 117, 121 extending and movable relative to the sleeve 118. The sleeve 118 may be inelastic and the respective elastic component 117, 121 may expand and contract in length within the sleeve 118 and may be confined within the sleeve 118 during extension from and contraction to the predetermined length. The sleeve 118 may define a first free end proximate the tensioning device 111 and may provide a robust attachment point on the respective connector 112a, 112b at a second end, cooperates with the elastic components 117, 121, and protects the elastic components 117, 121, while not inhibiting the tensioning operation of the adjustment system 110.

The sleeve 118 advantageously may define a gap or aperture 119 in an outer surface thereof through which at least a portion of the elastic components 117, 121 may be visible to a user. The aperture 119 may generally extend in a lateral direction and be shaped as a slot, and vertical inspection slots 440 (shown in FIG. 4C) may further be defined by and within the body of the sleeve 118. The sleeve 118 may define a reference against which a desired level of tension in the elastic components 117, 121 may be ascertained and obtained. In an exemplary embodiment the sleeve 118 is formed from a thermoplastic overmold material. It will be understood that the sleeve 118 need not be an overmolded or polymeric material, but rather may comprise any suitable configuration and material.

The vertical inspection slots 440 may be configured to align with vertically oriented tensioning indicia 120 provided on at least a surface of the elastic components 117, 121 when a desired degree of tensioning is reached or obtained. When the elastic components 117, 121 are tensioned by the tensioning device 111, the elastic components 117, 121 may become elongated due to their elasticity, and the tensioning indicia 120 provided at specific locations on the elastic components 117, 121 may become visible or exposed through the vertical inspection slots 440 as the tensioning indicia 120 translate relative to the sleeve 118. In this way, alignment of predetermined configurations of the tensioning indicia 120 with the vertical inspection slots 440 indicates to a user the current level of tension in the adjustment system 110, such that the tensioning device 111 can be actuated to a proper and precise degree.

The aperture 119 may be configured to reveal to a user other indicia 120 on the surface of the elastic components 117, 121, which may comprise colors, symbols, or other markings and may be seen or otherwise surmised to be lateral (requiring greater tension) or medial (requiring less tension) relative to indicia 120, directing a user whether more or less tension is needed in the tensioning device 111 for proper tension and fit based on a user's needs. Indicia 125 may be provided on the surface of the sleeve 118, alignment of the tensioning indicia 120 with which may further provide tensioning information to a user.

In an embodiment, the indicia 120 are provided on a predetermined location of the first and second elastic components 117, 121. The predetermined location may be analogous in the first and second components 117, 121 or may be different. The indicia 120 may be a vertical line printed or attached to an outward-facing surface of the attachment component 117, 121. The outward surface laterally of the indicia 120 may be a first color, such as red, and the surface medially may be the same or a different color. Thus when a second indicium 125 is provided on an external surface of the sleeve 118, alignment between the indicia 120, 125 indicates a desired degree of tension has been obtained.

Conversely, one of the colors adjacent the indicia 120 being aligned with the indicia 125 may indicate to the user that further adjustment is needed. For example, the first color may indicate a degree of overtension while a second color arranged opposite the first color may indicate a degree of undertension. The described embodiment of first and second colors is merely exemplary, and any suitable arrangement may be used. Colors, patterns, shapes, digital readouts, or any other suitable mechanism may instead be used to provide feedback ensuring proper adjustment. In embodiments, individual users may mark the elastic components to indicate a desired level of tension for their use for a particular task, in contrast to markings laid down for other tasks or by other users who may use the body interface 100 on subsequent shifts or tasks.

Figure 4A:
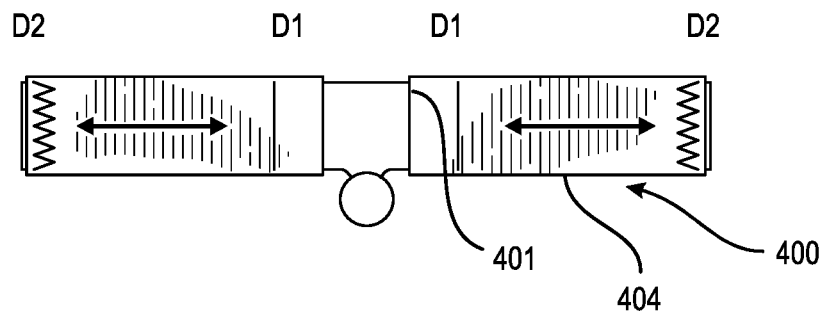
FIG. 4A illustrates a schematic view of the adjustment system in FIG. 1.
Figure 4B:
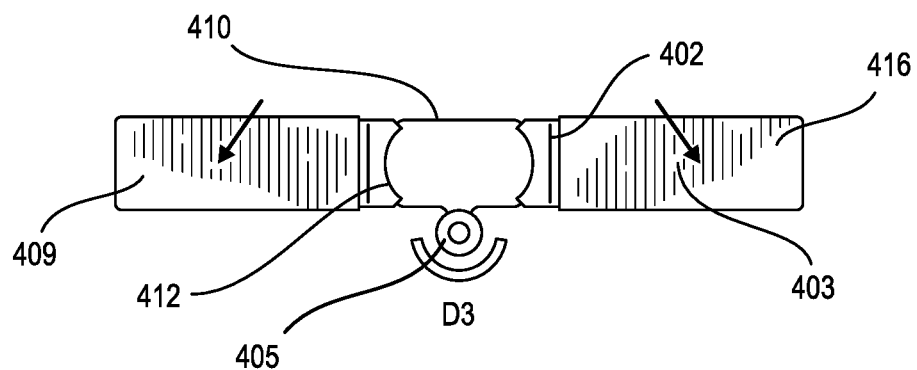
FIG. 4B illustrates a schematic view of an elastic component of the adjustment system of FIG. 4A.
Figure 4C:
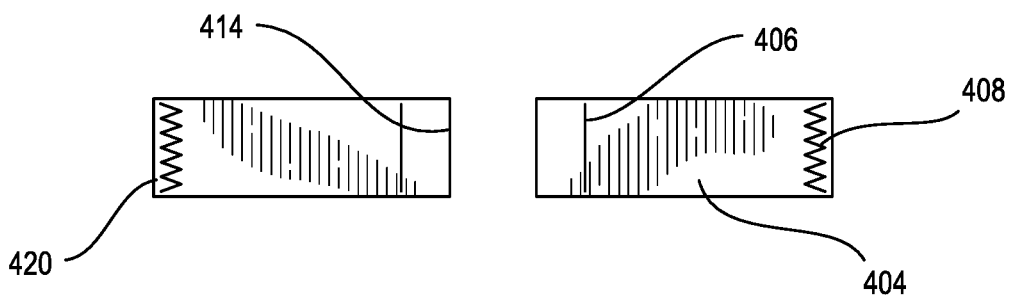
FIG. 4C illustrates a schematic view of an elastomeric overmold of the adjustment system of FIG. 4A.

The sleeve 118 and the elastic components 117, 121 attach at lateral extreme or second ends at a reinforced junction 420 (shown in FIG. 4C). The elastic components 117, 121 thus may have only a single degree of freedom in their movement relative to the sleeve 118. In embodiments, additional degrees of freedom are contemplated.

The sleeve 118 and the elastic components 117, 121 may attach proximate the reinforced junction 420 to first and second connectors 112a, 112b by a fastener 109, which may comprise a rivet, screw, plastic component, elastomeric component, or any other article or method for fastening the overmold sleeve 118 and the elastic components 117, 121 to the respective connector 112a, 112b. In other embodiments, the fastener 109 may be an adhesive applied along a length of the sleeve 118 and the elastic components 117, 121.

The first and second connectors 112a, 112b are anchored or biased in the second direction D2 by the attachments 150, 152 and may be variably biased in the first direction D1 by the adjustment system 110. The first and second connectors 112a, 112b are configured to translate or float relative to the frame 102 depending on the degree of tension from the adjustment system 110 along a predetermined path on a sliding track 114 connected to the posterior surface of the frame 102 by suitable methods. In embodiments, the sliding track 114 may be defined by the frame 102, for example by a slot or aperture formed within or through a thickness of the frame 102. While the second direction D2 is shown as being opposite the first direction D1 and generally horizontally relative to a user, the directions D1, D2 may extend in any suitable arrangement. The depicted embodiment of a sliding track 114 is merely exemplary and any suitable element or component that may serve to guide the connectors relative to the frame is contemplated.

As the first and second connectors 112a, 112b translate medially and laterally relative to the frame 102 in the directions D1, D2, they are better configured for positioning exoskeleton devices or other assistive devices over individual users' differing back and shoulder widths. The attachments 150, 152 may be exoskeleton devices that attach at apertures 113 on the first and second connectors 112a, 112b. The sliding track 114 may have lateral terminals 116 which provide a hard stop for each connector 112a, 112b at corresponding lateral portions of the frame 102 and corresponding to an end of the elastic components 117, 121 in the direction D2, preventing further lateral translation under bias from for example the attachments 150, 152, and medial terminals 129 preventing further medial translation under tension and corresponding to an end of the elastic components 117, 121 in the direction D1. The medial terminals 129 may additionally serve as guides for the elongate tensioning element 122 as it attaches between both of the elastic attachment components 117, 121 and the tensioning device 111 to form a circuit.

For additional stability, the frame 102 provides an upper translation slot 115 through which fasteners 106 of the first and second connectors 112a, 112b may secure. As shown in FIG. 1, the sliding track 114 extends obliquely relative to the upper translation slot 115. The fasteners 106 may secure the first and second connectors 112a, 112b in their vertical configuration regardless of the degree of tension applied by the tensioning device 111, and may serve to guide the respective connector 112a, 112b as it translates or floats relative to the frame 102. The fasteners 106 ensure that as the corresponding translation slots 115 are provided for each component of the adjustment system 110 (i.e. elastic components 117, 121), movement of the connectors 112a, 112b may be symmetric. Alternatively, the relative movement of the connectors 112a, 112b may be asymmetric or eccentric relative to one another depending on the manner in which the slots (relative length and/or direction of slots) and/or elastic components 117, 121 are arranged relative to one another (i.e., relative elasticities).

FIG. 2 depicts in plan view an anterior or user-facing side A of a body interface 200, including a vertical strut 201, a T-shaped junction 252 defined by and at an upper portion of a frame 202. The embodiment of a body interface 200 of FIG. 2 illustrates in additional detail a fastener 205 which connects a lumbar portion 204 with a frame 202. The frame 202 comprises left and right arms 234, 236 extending generally horizontally relative to the vertical strut 201, whereat series of apertures 250, 257 are defined for attaching elements of an adjustment system 210, such as slide tracks 214, and a tensioning device anchor 223 corresponding to the components described above regarding the embodiment of FIG. 1.

FIG. 3 depicts in perspective view an embodiment of a multi-component adjustment system in a body interface system 300 and arranged to cooperate with an exoskeleton device. A frame 302 comprises a vertical strut 303 as depicted in previous embodiments and may be covered by a comfortable cover 330, in this embodiment a thermoplastic elastomer overmold material. In other embodiments, the cover 330 may be formed of any suitable material. First and second connectors 306 are slidably attached to the frame 302 and may support attachments such as arm-assist devices 150, 152, over a user's shoulders and on a user's arms via multiple-degrees-of-freedom attachments 308.

The body interface system 300 may be supported on a user's body via, for example, arm straps 314, axillary straps 316, shoulder straps 311, and a lumbar belt 312. A skilled person will recognize that other arrangements of straps, assistive devices, and connectors may fit within the spirit and scope of the disclosure, and may benefit both structurally and functionally from the adjustment system providing easier, more accurate, and intuitive adjustment of one or more components for optimal operation and compatibility with a user.

A multi-component adjustment system 320 as described in previous embodiments may be arranged at a suitable location such as the center of the vertical strut 303 and at an upper portion of the frame 302, and may apply, in symmetrical manner, tension to one or more connectors 306 arranged over a user's left and right scapulae and arranged to translate or float along rails or other forms of a path defined by or on the frame 302.

As a tensioning device 325 of the adjustment system 320 applies tension by shortening a length of an elongate tensioning element which is routed in a circuit between the tensioning device 325 and corresponding elastic components 301, the connectors 306 may be drawn together medially in a symmetric manner and at equal rates against the lateral or outward bias from the attachments 150, 152 to which the elastic components 301 are anchored, configuring the system 300 for a user's specific dimensions in a simple and intuitive procedure. The adjustment procedure may be repeated as the body interface system 300 is donned by subsequent users such that each user may reliably obtain a desired configuration of the connectors 306 over their shoulders, ensuring optimal performance of the exoskeleton device by not allowing the connectors 306 to settle into a position of least resistance.

The operation of the adjustment system 320 of FIG. 3 may be better understood in reference to the embodiment shown in FIGS. 4A-4C, which demonstrates the operation of an adjustment system 400 according to the disclosure. The adjustment system 400 comprises, in the depicted embodiment, a dial-tensioning device 405 that cooperates with an elongate tensioning element 410, which may be a wire, cord, or any other material that suitable properties in an adjustment system.

The one or more components that are tensioned or adjusted by the adjustment system 400 may comprise one or more elastic components 403 and corresponding sleeves 404 attached to the elastic components 403 and defining within a thickness thereof a channel 414 configured to receive the elastic components 403. It will be understood that the channel 414 within the sleeve 404 need not entirely circumscribe the elastic component 403, but rather may cover or enclose only a portion of elastic component 403.

The elastic components 403 may define a reinforcement region 402 at a first or medial portion or end 401 of the elastic components 403, the reinforcement region 402 defining a guide or channel 412 in the first or medial end 401 for receiving the elongate tensioning element 410. The channel 412 may route or extend perpendicularly relative to the predetermined length of the elastic component 403. This allows the tensioning device 405 and the elastic components 403 to form a circuit. The formation of the circuit allows the elastic components 403 to be tensioned or adjusted simultaneously and/or symmetrically by the action of the single tensioning device 405. The reinforcement region 402 may comprise elastic material or may comprise substantially inelastic materials such as reinforced materials or thermoplastic overmolded materials for robust retention of the elongate tensioning element 410.

In the depicted embodiment, a user may tension the adjustment system 400 by rotating the tensioning device 405 in a first manner or counterclockwise direction D3, causing the length of a segment of the elongate tensioning element 410 to decrease, and forcing the elastic components 403 to move in a medial direction D1 relative to a frame or surface on which the adjustment system 400 is used. The movement can result from tensioning and elongation because of tensioning of the elastic components 403.

The dial-tensioning device 405 can be configured to lock at a desired position such that the length of the elongate tensioning element 410 remains unchanged until the tensioning device 405 is unlocked by a user, thereby preventing unwanted changes in the configuration of the adjustment system 400. Conversely, a second manner or clockwise direction may correspond to an increase in the length of the segment of the tensioning element 410.

Upon release of tension in the tensioning device 405, the elastic components 403 may compress and return to a shorter length under a lateral bias in the lateral direction D2, for example stemming from a tendency of the attachments to drift outwardly. When a lateral end 409 of the elastic components 403 is attached to an anchor such as an attachment component via a connector as depicted in previous embodiments, for example, the elastic components may be configured to naturally compress or relax to an original predetermined length in the absence of tension. The lateral bias from the anchor causes the medial ends 401 to move away from each other in the lateral direction D2, moving the elastic components 403 to a configuration suitable for a user with wider shoulders.

The elastic components 403 may be attached to the sleeves 404 at the lateral end 409 by a reinforced attachment region 408, which may utilize reinforcement stitching 420 or any other suitable means for attaching the elastic components 403 to the overmolded sleeves 404. These suitable means may include hook-and-loop fastener, elastomeric material, pins, staples, or any other suitable means.

To provide an indication of a current or desired level of tension in the adjustment system 400, indicia 416 may be provided on a surface of the elastic components 403, which indicia 416 may be visible through a vertical observation or viewing slot 406 defined in and by a surface of the sleeve 404. As a user tensions the adjustment system 400, the indicia 416 may become visible through the viewing slot 406, indicating to the user to stop applying tension as a desired and/or predetermined level of tension has been attained. The desired level of tension may correspond to a specific width defined by the arm attachments.

The desired amount of tension provided by the tensioning device 405 and the elasticity of the elastic components 403 may be configured by a clinician or engineer to have any advantageous arrangement. For instance, the adjustment system 400 may have extensive elongation relative to tension provided by the tensioning device 405, such that the distance over which corresponding attachment elements translate relative to a frame or surface is minimized. Alternatively, the elastic components 403 may have reduced elongation, such that movement of the elastic components 403 upon tensioning of the adjustment system 400 is more pronounced.

Tension and elongation may be fine-tuned and configured such that the indicia 416 are visible through the slot 406 when the proper amount of tension for an application of the adjustment system 400 has been attained. In embodiments in which both sides of the adjustment system 400 may be tensioned equally and simultaneously, the slot 406 and the indicia 416 may need to be provided on only one of the elastic components 403.

The structure and function of the adjustment system 400 may facilitate an adjustment or tensioning system which allows for one or more components, such as attachment elements in a body interface or straps of an orthopedic device, to be tensioned simultaneously and/or symmetrically, simplifying use and reducing cost and complexity of manufacture. It will be appreciated that the adjustment system can be provided with a single component to be tensioning, or may comprise two components arranged asymmetrically, or may comprise more than two components in any suitable configuration relative to the frame. The adjustment system has been described in the context of a body interface for an exoskeleton device and may be equally advantageous for tensioning one or more straps of a strap system in an orthopedic device, for example, such that tensioning may be accomplished easily and evenly. Other devices requiring adjustable degrees of tension in one or more components may likewise benefit from the disclosed features.

Figure 5:
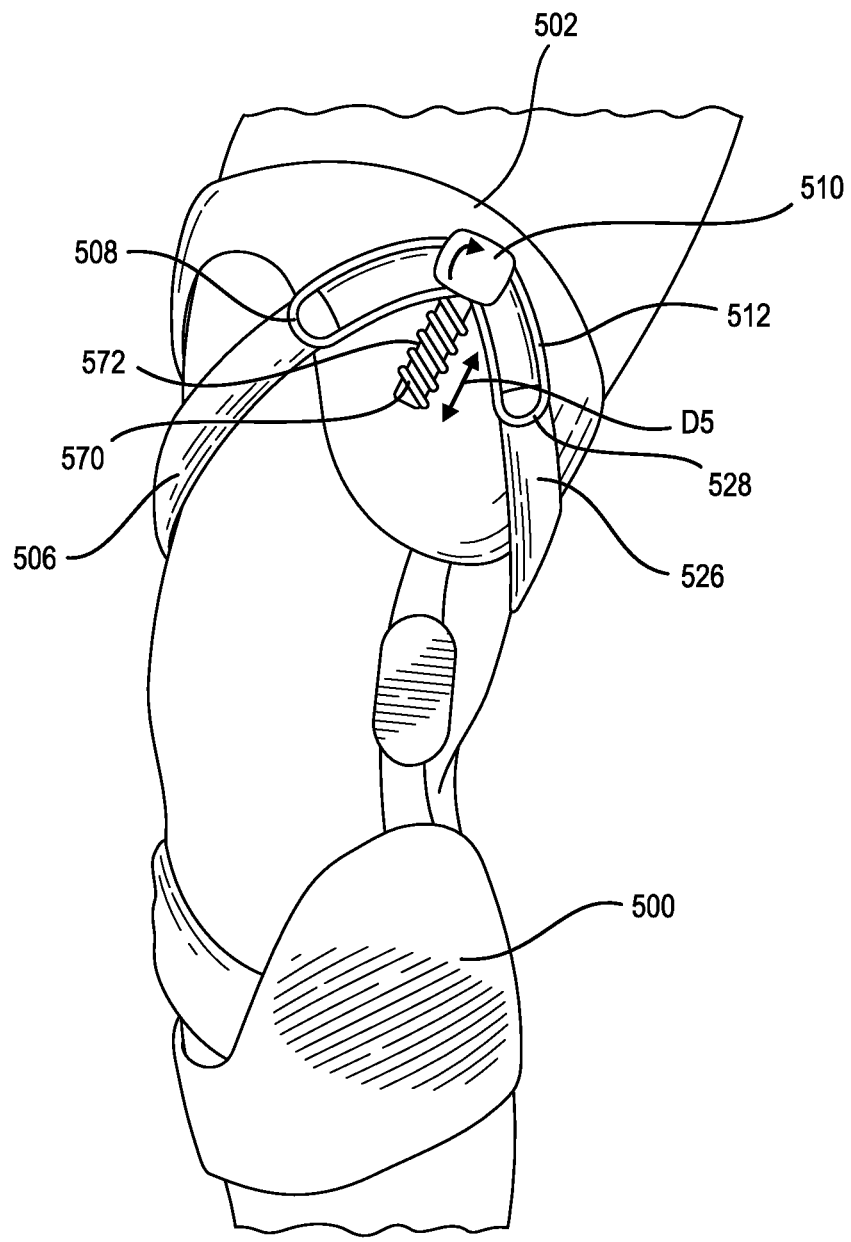
FIG. 5 illustrates a perspective schematic view of another embodiment of an adjustment system in cooperation with an orthopedic device such as a knee brace.

In an embodiment of an adjustment system applied to an orthopedic device, a knee brace 500, shown in perspective view in FIG. 5, a multi-component adjustment system 510 is arranged to tension or adjust simultaneously two straps 506, 526. In an embodiment the straps 506, 526 may be dynamic force straps arranged to spiral or helically extend about the knee and between upper and lower components of a frame 502. In the depicted embodiment, the adjustment system 510 is fixedly mounted on an upper component of the frame 502, making it more accessible to a user.

The adjustment system 510 may be arranged as a dial tensioner which may lengthen or shorten an elongate tensioning element 512 upon actuating the tensioner in a first or second manner. The tensioning element 512 may be provided as a cable, wire, or any other suitable material. The elongate tensioning element 512 is arranged to extend to and through channels defined in reinforced end portions 508, 528 of the dynamic force straps 506, 526, respectively, and to thereby define a circuit. As the adjustment system 510 is rotated in a direction, it may reduce the length of the circuit and thereby apply tension to the straps 506, 526 in a symmetrical and precise manner, easing adjusting and properly fitting the orthopedic device 500 to the user's individual dimensions, which may be dynamic. For example, swelling after an injury, operation, or use may cause the leg to increase or decrease in size, requiring a corresponding adjustment in the at least two straps 506, 526 for comfort and best fit. The adjustment system 510 allows for such adjustment to be simple, intuitive, and accurate.

In the depicted embodiment, the adjustment system 510 may be coupled with a constant-force spring 570. The constant-force spring 570 may be arranged to provide equal tensioning between the two straps 506, 526, by providing an equal degree of resistance throughout an entirety of tension applied to the adjustment system 510. The adjustment system 510 may be slidably mounted on a track 572 defined by and/or within the frame 502 of the orthopedic device 500, with compression applied to the constant-force spring 570 as greater tension is applied, causing the adjustment system 510 to slide within the track 572 and to compress the constant-force spring 570. The track 572 may be defined by or attached to a shell of the orthopedic device 500.

The track 572 may be defined in a direction relative to the attachment between the adjustment system 510 and the straps 506, 526 to provide a symmetrical and equal adjustment of the length and tension of the straps 506, 526 as the tension is increased. This arrangement advantageously allows the adjustment system 510 to provide greater accuracy and intuitiveness to the adjustment process. The straps 506, 526, track 572, and constant-force spring 570 are not limited to the depicted configuration, but rather may be arranged in any advantageous configuration. For example, the constant-force spring 570 and the track 572 may be arranged above or proximal relative to the adjustment system 510, with increased tension stretching rather than compressing a constant-force spring 570. Alternatively, the constant-force spring 570 may be replaced by another device having dynamic force, or the track 572 may be provided without a spring.

The adjustment system described herein overcomes numerous challenges in the field of tensioning systems, body interfaces, exoskeletons, orthopedic and prosthetic devices, medical devices, and other devices utilizing tensioning systems by providing a more simple, effective, and intuitive system for providing a desired degree of tension in devices with at least one component requiring tension. By using the adjustment system, body interfaces, exoskeletons, orthopedic devices, and other devices utilizing the adjustment system may enjoy reduced costs and complexities of manufacturing and better compliance from users.

Additionally, the adjustment system of the embodiments advantageously provides for more accurate adjustment of an adjustment system by providing features allowing for increased precision in adjusting one or more components. The indicia provided on elastic components and corresponding sleeves allow for tensioning to be conducted to discrete and/or predetermined levels with ease by a user.

While the disclosure discusses embodiments for a body interface cooperating with an upper-body exoskeleton and an adjustment or tensioning system for an orthopedic device, embodiments of the disclosure may be used with body interfaces and orthopedic, prosthetic, medical, and other devices attaching to other limbs, joints and anatomical portions including the torso, hip, knee, and foot/ankle. Further, while the embodiments of the disclosure describe attachment elements that may be tensioned to translate relative to a frame or structure in predetermined directions, it is to be understood that the adjustment system may tension one or more components to move in any direction or combination of directions advantageous for a particular application.

Not necessarily all such objects or advantages may be achieved under any embodiment of the disclosure. Those skilled in the art will recognize that the invention may be embodied or carried out to achieve or optimize one advantage or group of advantages as taught without achieving other objects or advantages as taught or suggested.

The skilled artisan will recognize the interchangeability of various components from different embodiments described. Besides the variations described, other known equivalents for each feature can be mixed and matched by one of ordinary skill in this art to construct an adjustment system or a body interface utilizing the adjustment system under principles of the present invention. Therefore, the embodiments described may be adapted to body interfaces and adjustment or tensioning systems for securing, supporting or cooperating with a variety of exoskeleton devices and other orthopedic, prosthetic, and medical devices.

Although this invention has been disclosed in certain preferred embodiments and examples, it nevertheless will be understood by those skilled in the art that the adjustment system embodiments extend beyond the disclosed embodiments to other alternative embodiments and/or uses of the adjustment system and obvious modifications and equivalents. It is intended that the scope of the present adjustment system disclosed should not be limited by the disclosed embodiments described above but should be determined only by a fair reading of the claims that follow.

The invention claimed is:

1. An adjustment system for mounting on a body interface adapted for being worn by a user, the body interface defines at least one upper translation slot, the adjustment system comprising:
   a tensioning device arranged to be fixedly secured to the body interface and having a housing and a cable receivable within the housing with a segment adjustable in length extending from the housing, the tensioning device configured for reducing a length of the segment of the cable extending from the housing due to actuation of the tensioning device in a first manner, and for lengthening the length of the segment of the cable extending from the housing due to actuation of the tensioning device in a second manner;
   at least one elastic component having a first end securing to the cable, the cable routing through the first end of the at least one elastic component perpendicularly relative to a predetermined length of the at least one elastic component, the at least one elastic component elastically extendable in length from and contractable to the predetermined length;

at least one connector securing to and at a second end of the at least one elastic component, the at least one connector configured to slidably connect to the body interface along a predetermined path defined by the body interface extending in a first direction directed toward the tensioning device and a second direction directed away from the tensioning device;

at least one sliding track defined by or attached to the body interface along which the at least one connector engages and is arranged to slide horizontally between the first and second directions;

a first medial terminal and a first lateral terminal located at medial and lateral ends, respectively, of the at least one sliding track, the first medial terminal and the first lateral terminal being arranged to define a hard stop in the first and second directions, respectively, of the at least one connector, wherein the first medial terminal guides the cable horizontally above the tensioning device and toward the first lateral terminal as the cable extends over or about the first medial terminal;

at least one sleeve extending about the at least one elastic component as the cable is actuated by the tensioning device, the at least one elastic component movable relative to the at least one sleeve;

wherein the at least one sleeve has a first end free from the at least one elastic component, and the at least one sleeve has a second end attached to the at least one connector such that the at least one sleeve and the at least one elastic component terminate at the second ends thereof at the at least one connector;

wherein the at least one elastic component biases the at least one connector in the first direction and contracts to the predetermined length at an end of the first direction, the at least one elastic component elastically resists movement of the at least one connector and elastically extends from the predetermined length in the second direction;

wherein the at least one connector includes at least one fastener located above the at least one sliding track, the at least one fastener arranged to engage the at least one upper translation slot of the body interface and maintain the at least one connector in a vertical configuration, the at least one sliding track extending obliquely relative to the at least one upper translation slot.

2. The adjustment system of claim 1, wherein the at least one elastic component comprises first and second elastic components located on opposite sides of the tensioning device, the cable securing to both the first and second elastic components and forming a circuit therewith such that actuation of the tensioning device in the first manner simultaneously draws both the first and second elastic components in said first direction.

3. The adjustment system of claim 2, wherein the at least one connector comprises first and second connectors connected to the first and second elastic components, respectively.

4. The adjustment system of claim 2, wherein the tensioning device is arranged to be centrally located between the first and second elastic components, the predetermined length of each of the first and second elastic components is the same.

5. The adjustment system of claim 1, wherein the at least one sleeve is inelastic and the at least one elastic component is arranged to expand and contract in length within the at least one sleeve.

6. The adjustment system of claim 5, wherein the at least one elastic component is confined within the at least one sleeve during extension from and contraction in length to the predetermined length.

7. The adjustment system of claim 1, wherein the at least one elastic component has a reinforcement region at the first end and formed from an inelastic material, the reinforcement region is arranged for the cable to route therethrough perpendicularly relative to the predetermined length of the at least one elastic component.

8. The adjustment system of claim 7, wherein the reinforcement region is formed from a thermoplastic material.

9. The adjustment system of claim 1, wherein the at least one elastic component is defined by at least one segment of elastic material.

10. The adjustment system of claim 1, wherein the at least one sleeve defines a channel within a thickness thereof arranged to receive the at least one elastic component.

11. The adjustment system of claim 1, wherein the at least one sleeve comprises at least one aperture configured to expose at least a portion of the at least one elastic component and through which indicia on the at least one elastic component are exposed.

12. The adjustment system of claim 1, wherein the at least one connector is arranged to transmit a load to the body interface and secure to at least one assistive device.

13. The adjustment system of claim 1, wherein the cable extends over the first medial terminal to connect to the at least one elastic component.

* * * * *